United States Patent
Boatman

(10) Patent No.: US 8,911,399 B2
(45) Date of Patent: Dec. 16, 2014

(54) WEEPING BALLOON CATHETER

(75) Inventor: Scott E. Boatman, Bloomington, IN (US)

(73) Assignee: Cook Medical Technologies LLC, Bloomington, NJ (US)

( * ) Notice: Subject to any disclaimer, the term of this patent is extended or adjusted under 35 U.S.C. 154(b) by 199 days.

(21) Appl. No.: 13/221,384

(22) Filed: Aug. 30, 2011

(65) Prior Publication Data
US 2011/0313400 A1 Dec. 22, 2011

Related U.S. Application Data

(63) Continuation of application No. 12/411,106, filed on Mar. 25, 2009, now Pat. No. 8,034,022.

(60) Provisional application No. 61/043,208, filed on Apr. 8, 2008.

(51) Int. Cl.
*A61M 29/00* (2006.01)
*A61M 25/10* (2013.01)

(52) U.S. Cl.
CPC ..... *A61M 25/1011* (2013.01); *A61M 2025/105* (2013.01); *A61M 2206/20* (2013.01); *A61M 2025/1013* (2013.01); *A61M 25/104* (2013.01)
USPC .............. 604/101.01; 604/96.01; 604/101.02; 604/101.03; 604/103.01; 604/103.02; 604/103.03; 604/103.05; 604/103.06; 604/103.07; 604/103.08

(58) Field of Classification Search
CPC .................................................... A61M 25/104
USPC ................. 604/96.01, 10.03, 103.05–103.08, 604/101.01–101.03, 509
See application file for complete search history.

(56) References Cited

U.S. PATENT DOCUMENTS

| 4,571,240 A | 2/1986 | Samson et al. ................... 604/96 |
| 4,744,366 A | 5/1988 | Jang .............................. 128/344 |

(Continued)

FOREIGN PATENT DOCUMENTS

| DE | 4225553 C1 | 5/1994 |
| EP | 1230944 A2 | 1/2002 |

(Continued)

OTHER PUBLICATIONS

Boatman, U.S. Appl. No. 13/221,403, filed Aug. 30, 2011.

(Continued)

*Primary Examiner* — Edelmira Bosques
(74) *Attorney, Agent, or Firm* — Brinks Gilson & Lione

(57) ABSTRACT

Balloon catheters, and methods of treatment therewith, are provided including an inflatable first balloon at least partially enclosed by an expandable second balloon that has holes. The annular space between the first balloon and the second balloon is configured to promote delivery of the fluid evenly through holes in the second balloon to avoid problems of underloading and/or overloading. Preferably, the annular space is in communication with the holes, and the annular space is configured to receive and then to release and distribute the fluid via the holes in a substantially uniform manner such that even amounts of fluid are released in the distal and proximal holes. The first balloon may have various configurations including being tapered relative to the second balloon. The second balloon may also be tapered accordingly. The device may also include raised portions disposed in the annular space and configured to define channels having various configurations.

20 Claims, 6 Drawing Sheets

(56) References Cited

U.S. PATENT DOCUMENTS

| | | | |
|---|---|---|---|
| 4,994,033 A | 2/1991 | Shockey et al. | 604/101 |
| 5,049,132 A * | 9/1991 | Shaffer et al. | 604/101.02 |
| 5,098,381 A | 3/1992 | Schneider | 604/96 |
| 5,112,305 A | 5/1992 | Barath et al. | 604/96 |
| 5,213,576 A | 5/1993 | Abiuso et al. | 604/96 |
| 5,232,444 A | 8/1993 | Just et al. | 604/96 |
| 5,232,445 A | 8/1993 | Bonzel | 604/96 |
| 5,236,413 A | 8/1993 | Feiring | 604/21 |
| 5,273,536 A | 12/1993 | Savas | 604/96 |
| 5,295,962 A | 3/1994 | Crocker et al. | 604/101 |
| 5,304,135 A | 4/1994 | Shonk | 604/101 |
| 5,318,531 A | 6/1994 | Leone | 604/96 |
| 5,338,298 A | 8/1994 | McIntyre | 604/96 |
| 5,342,305 A | 8/1994 | Shonk | 604/101 |
| 5,380,304 A | 1/1995 | Parker | 604/282 |
| 5,447,497 A | 9/1995 | Sogard et al. | 604/101 |
| 5,458,568 A | 10/1995 | Racchini et al. | 604/19 |
| 5,536,252 A | 7/1996 | Imran et al. | 604/101 |
| 5,547,472 A | 8/1996 | Onishi et al. | 604/93 |
| 5,569,184 A | 10/1996 | Crocker et al. | 604/53 |
| 5,571,089 A | 11/1996 | Crocker | 604/102 |
| 5,611,775 A | 3/1997 | Machold et al. | 604/53 |
| 5,645,789 A | 7/1997 | Roucher, Jr. | 264/529 |
| 5,669,874 A | 9/1997 | Feiring | 604/21 |
| 5,685,847 A | 11/1997 | Barry | 604/96 |
| 5,690,642 A | 11/1997 | Osborne et al. | 606/108 |
| 5,704,913 A | 1/1998 | Abele et al. | 604/101 |
| 5,797,878 A | 8/1998 | Bleam | 604/196 |
| 5,800,392 A | 9/1998 | Racchini | 604/96 |
| 5,814,061 A | 9/1998 | Osborne et al. | 606/194 |
| 5,823,996 A * | 10/1998 | Sparks | 604/103.01 |
| 5,866,561 A | 2/1999 | Ungs | 514/182 |
| 6,010,521 A | 1/2000 | Lee et al. | 606/194 |
| 6,048,332 A | 4/2000 | Duffy et al. | 604/96 |
| 6,126,634 A | 10/2000 | Bagaoisan et al. | 604/96 |
| 6,129,737 A | 10/2000 | Hamilton et al. | 606/194 |
| 6,149,641 A | 11/2000 | Ungs | 604/501 |
| 6,221,043 B1 | 4/2001 | Fischell et al. | 604/103.07 |
| 6,258,108 B1 | 7/2001 | Lary | 606/159 |
| 6,280,411 B1 | 8/2001 | Lennox | 604/103.05 |
| 6,344,028 B1 | 2/2002 | Barry | 604/96.01 |
| 6,383,212 B2 | 5/2002 | Durcan et al. | 623/1.11 |
| 6,409,741 B1 | 6/2002 | Crocker et al. | 606/192 |
| 6,413,203 B1 | 7/2002 | Sahatjian | 600/3 |
| 6,488,653 B1 | 12/2002 | Lombardo | 604/103.06 |
| 6,517,533 B1 | 2/2003 | Swaminathan | 606/20 |
| 6,540,734 B1 | 4/2003 | Chiu et al. | 604/508 |
| 6,544,221 B1 | 4/2003 | Kokish et al. | 604/103.01 |
| 6,544,223 B1 | 4/2003 | Kokish | 604/103.01 |
| 6,554,841 B1 | 4/2003 | Yang | 606/108 |
| 6,623,452 B2 | 9/2003 | Chien et al. | 604/103.01 |
| 6,626,861 B1 | 9/2003 | Hart et al. | 604/96.01 |
| 6,659,977 B2 | 12/2003 | Kastenhofer | 604/96.01 |
| 6,696,121 B2 | 2/2004 | Jung, Jr. et al. | 428/35.7 |
| 6,733,474 B2 | 5/2004 | Kusleika | 604/103.01 |
| 6,878,329 B2 | 4/2005 | Blankenship et al. | 264/294 |
| 6,881,216 B2 | 4/2005 | Di Caprio et al. | 606/192 |
| 6,896,842 B1 | 5/2005 | Hamilton et al. | 264/515 |
| 6,939,320 B2 | 9/2005 | Lennox | 604/103.02 |
| 6,942,680 B2 | 9/2005 | Grayzel et al. | 606/194 |
| 6,960,187 B2 | 11/2005 | Kastenhofer | 604/103.06 |
| 6,989,025 B2 | 1/2006 | Burgmeier et al. | 623/1.11 |
| 7,048,714 B2 | 5/2006 | Richter | 604/103.02 |
| 7,052,510 B1 | 5/2006 | Richter | 623/1.11 |
| 7,094,765 B1 | 8/2006 | Iversen et al. | 514/44 |
| 7,115,299 B2 | 10/2006 | Kokish | 427/2.24 |
| 7,179,251 B2 | 2/2007 | Palasis | 604/509 |
| 7,179,345 B2 | 2/2007 | Shkolnik | 156/293 |
| 7,225,518 B2 | 6/2007 | Eidenschink et al. | 29/283.5 |
| 8,034,022 B2 | 10/2011 | Boatman | 604/96.01 |
| 2004/0122457 A1 | 6/2004 | Weber | 606/159 |
| 2004/0172121 A1 | 9/2004 | Eidenschink et al. | 623/1.11 |
| 2004/0181252 A1 | 9/2004 | Boyle et al. | 606/194 |
| 2004/0243158 A1 | 12/2004 | Konstantino et al. | 606/159 |
| 2004/0260239 A1 | 12/2004 | Kusleika | 604/101.02 |
| 2005/0261722 A1 | 11/2005 | Crocker et al. | 606/192 |
| 2006/0200110 A1 | 9/2006 | Lentz et al. | 604/524 |
| 2006/0224115 A1 | 10/2006 | Willard | 604/103.04 |
| 2006/0258987 A1 | 11/2006 | Lentz et al. | 604/164.01 |
| 2006/0269587 A1 | 11/2006 | Iversen et al. | 424/426 |
| 2006/0287665 A1 | 12/2006 | Burton et al. | 606/192 |
| 2007/0118076 A1 | 5/2007 | Lim et al. | 604/103.06 |
| 2007/0135830 A1 | 6/2007 | Schaeffer | 606/192 |
| 2008/0300610 A1 | 12/2008 | Chambers | 606/159 |
| 2010/0069900 A1 | 3/2010 | Shirley et al. | 606/21 |
| 2010/0331817 A1 | 12/2010 | Schaeffer et al. | 604/509 |

FOREIGN PATENT DOCUMENTS

| | | |
|---|---|---|
| WO | WO 2006/074256 A1 | 7/2006 |
| WO | WO 2006/114783 A2 | 11/2006 |
| WO | WO 2009/033026 A1 | 3/2009 |
| WO | WO 2009/036135 A1 | 3/2009 |

OTHER PUBLICATIONS

Saab, Mark A., Applications of High-Pressure Balloons in the Medical Device Industry, dated 1999, pp. 1-19, Advanced Polymers, Inc., http//www.ventionmedical.com/Documents/MedicalBalloonPaper.pdf.

Medical Balloons, dated 2007, pp. 1-7, Advanced Polymers Inc., http://www.advpoly.com/Products/MedicalBalloons/ (posted on or before Apr. 2, 2008).

* cited by examiner

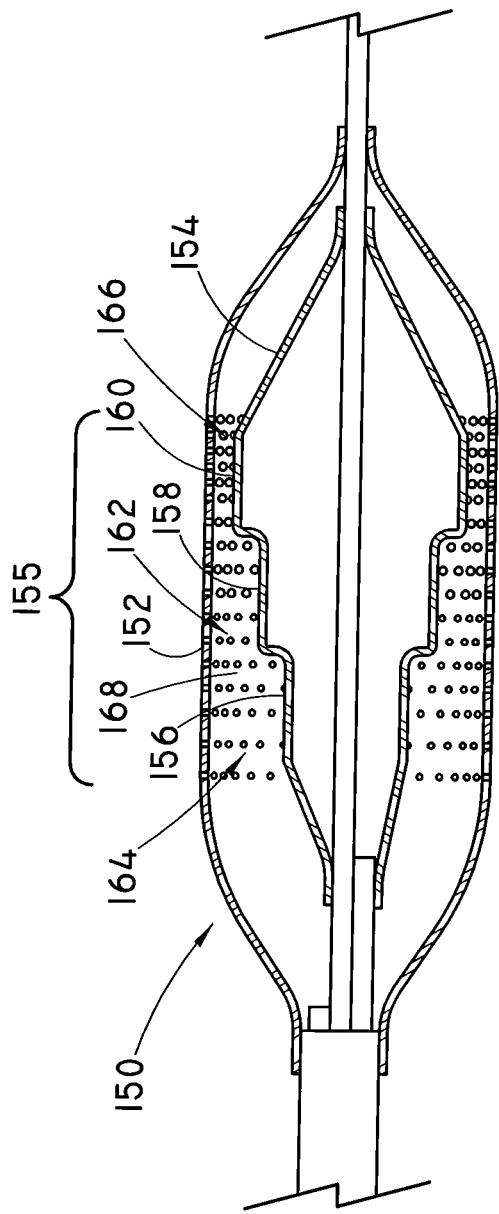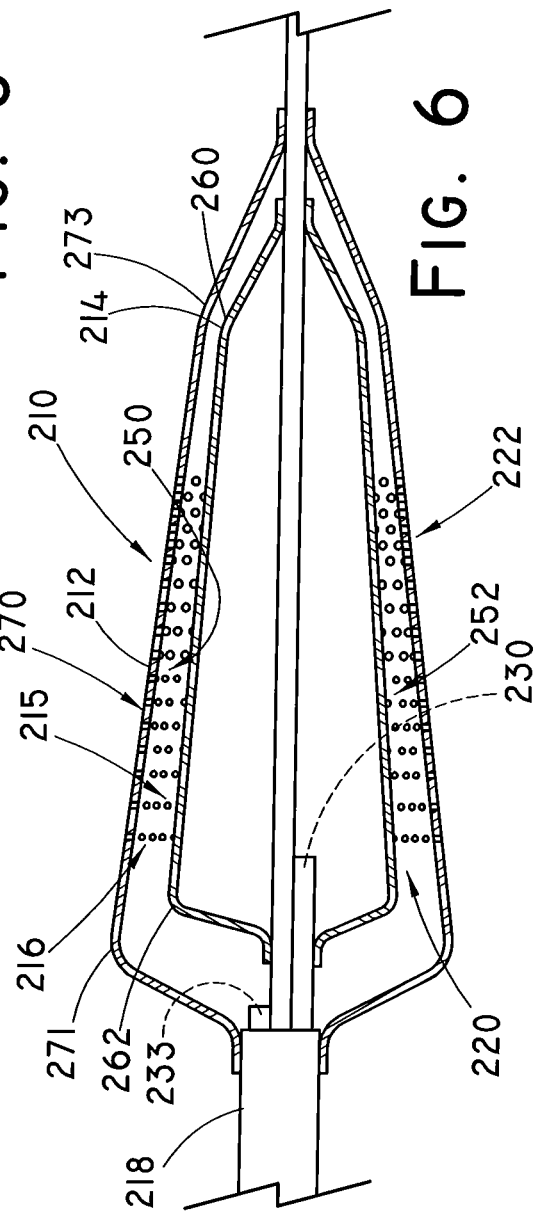

WEEPING BALLOON CATHETER

CROSS-REFERENCE TO RELATED APPLICATIONS

This application is a continuation of prior U.S. patent application Ser. No. 12/411,106, filed Mar. 25, 2009, which claims priority and the benefit of provisional U.S. Patent Application Ser. No. 61/043,208, filed Apr. 8, 2008, both of which are incorporated herein by reference in their entirety.

TECHNICAL FIELD

The present application relates to medical catheters configured to release a therapeutic agent. More particularly, the present application relates to medical multiple balloon catheters useful in the local administration of a therapeutic agent within a body vessel, as well as methods for the local administration of a therapeutic agent.

BACKGROUND

Localized administration of therapeutic agents within a body vessel can be advantageous for treatment of a variety of medical conditions. Although such medical conditions can be treated by the general systemic administration of a therapeutic agent, systemic administration of some therapeutic agents can not only result in the unnecessary absorption of the therapeutic agent by tissue outside an intended point of treatment, but also require administration of a greater dose of the therapeutic agent than necessary to compensate for the dissipated therapeutic agent. Accordingly, the treatment of many conditions requires local delivery of the therapeutic agent to a particular portion of internal body tissue, without dissipating the therapeutic agent to the tissue surrounding the particular portion of tissue.

To aid site-specific localized treatment, percutaneous delivery systems such as medical catheters can be used to deliver a therapeutic agent to the target site within a body vessel with minimal invasiveness. Medical catheters permit the delivery of the therapeutic agent from the medical catheter placed within the body vessel proximate the desired treatment site. The delivery of the therapeutic agent from the medical catheter can occur before, during and/or after a procedure such as percutaneous transluminal coronary angioplasty (PTCA), a technique used to dilate stenotic portions of blood vessels. The medical catheter can be adapted to perform a PTCA procedure and locally deliver the therapeutic agent to the site of the procedure. During PTCA, a medical balloon catheter is threaded into and through a body vessel lumen along a wire guide and positioned at a stenosis or other point of treatment, where the balloon is inflated to dilate the target site of the body vessel lumen. After treatment, the balloon is deflated and the catheter is removed from the target site and the patient's lumen, thereby allowing blood to freely flow through the unrestricted lumen.

At times after PCTA the treated portions of the body vessel can have a reoccurrence of constrictions or blockages. This phenomenon is called restenosis, which is the reoccurrence of stenosis at the treated site within the body vessel that can be caused by the body responding to the surgical procedure. Restenosis of the body vessel commonly develops over several months after the procedure, which can require another angioplasty procedure or a surgical by-pass operation. Proliferation and migration of smooth muscle cells (SMC) from the media layer of the lumen to the intima can cause an excessive production of extra cellular matrices (ECM), which is believed to be one of the leading contributors to the development of restenosis. The extensive thickening of tissues narrows the lumen of the blood vessel, constricting or blocking the blood flow through the vessel.

Therapeutic agents can limit or prevent restenosis. The therapeutic agents can be locally delivered with PTCA from a catheter and/or by placement of a stent configured to release the therapeutic agent after the PTCA procedure. Procedures involving medical balloon catheters can also be used in combination with the placement of stents, synthetic vascular grafts or administration of therapeutic agents, during the PTCA procedure to reduce or eliminate the incidence of restenosis.

Medical balloon catheters have been developed to administer the therapeutic agent locally to tissue while dilating a body vessel. For instance, a medical balloon catheter can include two concentrically arrayed coaxial balloons at the distal end of a double balloon catheter, also called a balloon-inside-a-balloon design. The outer balloon can include one or more perforations or holes to locally administer a therapeutic agent, while the inner balloon provides the dilatation and/or sealing of the body vessel lumen.

Nevertheless, localized administration of therapeutic agents evenly within a body vessel with a double balloon catheter can be difficult. In particular, during administration of the therapeutic agent, more of the therapeutic agent can diffuse out of the outer balloon holes at the proximal end of the outer balloon than from the outer balloon holes positioned nearer the distal end of the outer balloon. This can result in administering the therapeutic agent unevenly along the length of the outer balloon, possibly due to fluid pressure losses between the annular spaces along the length of the balloon due to the wall shear stresses on the fluid flowing between the balloons. Thus, there remains a need for a multiple balloon catheter for expanding a body vessel and locally administering medication evenly to the body vessel for an intended medical application. Also, there remains a need for a multiple balloon catheter for expanding a body vessel and locally administering medication to the body vessel evenly along the length of the balloon catheter to avoid overloading of the therapeutic agent at the proximal end and/or underloading of the therapeutic agent at the distal end of the catheter.

SUMMARY

The present disclosure describes multiple-balloon fluid delivery catheter configurations that release a fluid in a desired manner by providing preferred configurations of the annular space between an inner balloon and an outer balloon around the catheter. The multiple-balloon catheters or weeping balloon catheters may include a catheter shaft having a perforated, expandable outer balloon disposed around at least a portion of an inflatable inner balloon. The balloons in the respective inflated and expanded configurations define an annular lumen. The annular lumen is in communication with a fluid delivery lumen extending along the catheter shaft and the holes of the outer balloon. Fluid passed through the fluid delivery lumen in the catheter shaft and the annular lumen may be released through the holes of the outer balloon.

The configuration of the annular lumen are preferably selected to provide a substantially equal rate, volume, pressure, or any combination, of fluid flow through the holes of the outer balloon at a fixed fluid delivery pressure at the proximal end of the catheter shaft. By varying the configuration of at least one of the inner balloon, the outer balloon, and/or attachments therebetween, the annular lumen is then configured to promote delivery of the fluid evenly through the plurality of holes in the outer balloon. Preferably, there will not be more fluid released at the proximal end of the porous region of the outer balloon compared to the distal end of the porous region the outer balloon. This ensures that the point of treatment within the body vessel is receiving equal amounts of fluid along the outer balloon, thereby preventing wasteful release of excess fluid within the body vessel.

In one embodiment, a balloon catheter for delivering a fluid into a body vessel includes a catheter shaft, a first balloon, and a second balloon. The catheter shaft extends along a longitudinal axis. The first balloon includes a middle working region and is mounted on the catheter shaft. The second balloon is mounted around at least a portion of the first balloon. The second balloon has a middle working length and a plurality of holes formed in the middle working length to define a perforated portion. The holes are disposed along the circumferential surface of the balloon, and preferably along the middle portion. The holes can be uniform in size and frequency, but also can vary in size and frequency.

Each of the first and second balloons is movable to an expanded configuration to define an annular space between the first and second balloons. The annular space is in communication with the plurality of holes. The annular space can have an annular working region disposed between the perforated portion of the middle working length of the second balloon and a corresponding portion of the middle working region of the first balloon. The annular working region can have an increasingly smaller cross-sectional area along the longitudinal axis in a distal direction.

Various configurations are provided to vary the cross sectional area of the annular working region between the first balloon and second balloon in order to promote delivery of the fluid evenly through the plurality of holes.

In one aspect, the first balloon in the expanded configuration can include an increasingly larger cross-sectional area along the middle working region in the distal direction. Alternatively, the first balloon in the expanded configuration can include an increasingly smaller cross-sectional area along the middle working region in the distal direction. Alternatively, the first balloon in the expanded configuration can have a uniform taper along the middle working region.

In another aspect, the second balloon in the expanded configuration can include a tapering surface having an increasingly smaller, or larger, cross-sectional area along the middle working length in the distal direction. In one example, the first balloon in the expanded configuration can be cylindrical having a uniform cross-sectional area along the middle working region. In another example, the first balloon in the expanded configuration can include a tapering surface having an increasingly smaller, or larger, cross-sectional area along the middle working region in the distal direction. The taper of the tapering surface of the second balloon can be greater, or smaller, than the taper of the tapering surface of the first balloon.

The above, as well as other advantages of the present invention, will become readily apparent to those skilled in the art from the following detailed description of a preferred embodiment when considered in the light of the accompanying drawings.

BRIEF DESCRIPTION OF THE DRAWINGS

FIG. 5 is a side view of another multiple-balloon catheter, depicting an inner balloon having a stepped configuration.
FIG. 6 is a side view of another multiple-balloon catheter, depicting an outer balloon having a taper.

DETAILED DESCRIPTION

As used herein, the term "implantable" refers to an ability of a medical device to be positioned at a location within a body, such as within a body vessel. Furthermore, the terms "implantation" and "implanted" refer to the positioning of a medical device at a location within a body, such as within a body vessel.

The term "biocompatible" refers to a material that is substantially non-toxic in the in vivo environment of its intended use, and that is not substantially rejected by the patient's physiological system (i.e., is non-antigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of patients, will not cause an undesirably adverse, long-lived or escalating biological reaction or response, and is distinguished from a mild, transient inflammation which typically accompanies surgery or implantation of foreign objects into a living organism.

As used herein, the term "body vessel" means any body passage lumen that conducts fluid, including but not limited to blood vessels, esophageal, intestinal, billiary, urethral and ureteral passages.

The medical devices of the embodiments described herein can be oriented in any suitable absolute orientation with respect to a body vessel. The recitation of a "first" direction is provided as an example. Any suitable orientation or direction can correspond to a "first" direction. For example, the first direction can be a radial direction in some embodiments.

Figure 1:
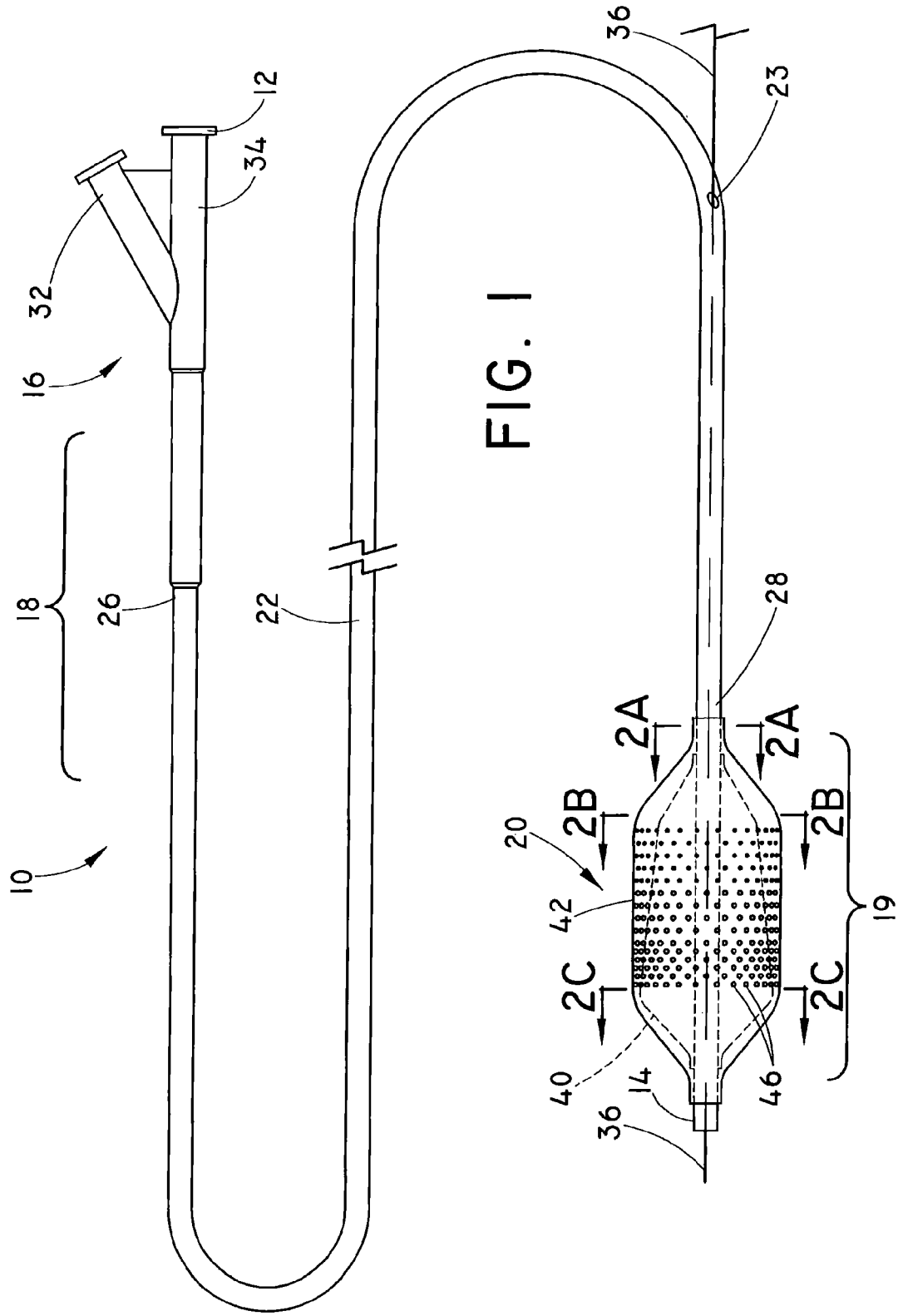
FIG. 1 is a perspective view of a multiple-balloon catheter.

FIG. 1 illustrates an exemplary embodiment of a medical device comprising a multiple-balloon catheter 10 or weeping balloon catheter. The multiple-balloon catheter 10 extends from a proximal end 12 to a distal end 14. Therebetween, the multiple-balloon catheter 10 includes a manifold 16 located toward a proximal region 18 of the multiple-balloon catheter 10 and a multiple-balloon assembly 20 at a distal region 19 of the multiple-balloon catheter 10. The manifold 16 is operatively joined to a catheter shaft 22 in the proximal region 18, with the catheter shaft 22 extending from a proximal end 26 to a distal end 28. The manifold 16 can include a lateral injection port 32 and an inflation port 34. The catheter shaft 22 can include an inflation lumen 30, a fluid delivery lumen 33 spaced from the inflation lumen 30, and a wire guide lumen 38. The catheter shaft 22 can also include one or more conventional fittings and/or adapters between the manifold 16 and the proximal end 26 of the catheter shaft 22. The multiple-balloon catheter 10 can be a "short wire" system having a wire guide port 23 within an intermediate region of the catheter shaft 22, providing access to a wire guide lumen 38 extending through the catheter shaft 22 from the wire guide port 23 to the distal end 14 of the multiple-balloon catheter shaft 10, as shown in FIG. 1. Optionally, the multiple-balloon catheter 10 can be an "over the wire" system with the wire guide port 23 positioned as part of the manifold 16. That is, the manifold 16 can include the wire guide port 23 in addition to the inflation port 34 and the injection port 32.

The distal region 19 of the multiple-balloon catheter 10 includes a perforated second balloon 42 radially disposed around at least a portion of a first balloon 40. The first balloon 40 is preferably non-porous and in fluid communication with the inflation port 34 through the body of the catheter shaft 22. The second balloon 42 includes a plurality of holes 46 and is in fluid communication with the injection port 32 through the catheter shaft 22 and separated from both the first balloon 40 and the inflation port 34.

In a preferred embodiment shown in FIG. 1, the first balloon 40 is a tapered inner balloon, having a portion with an increasingly larger cross-sectional area moving distally along the longitudinal axis 24, and the second balloon 42 is an outer cylindrical balloon. Optionally, multiple inner balloons, each having a uniform cross-sectional area, a tapering cross-sectional area, or both, can be arranged within the outer balloon, where much like the stepped configuration embodiment, described in more detail below, the general cross-sectional area of each balloon is increasingly larger moving along the longitudinal axis in the distal direction to generally define a taper.

Figure 3:
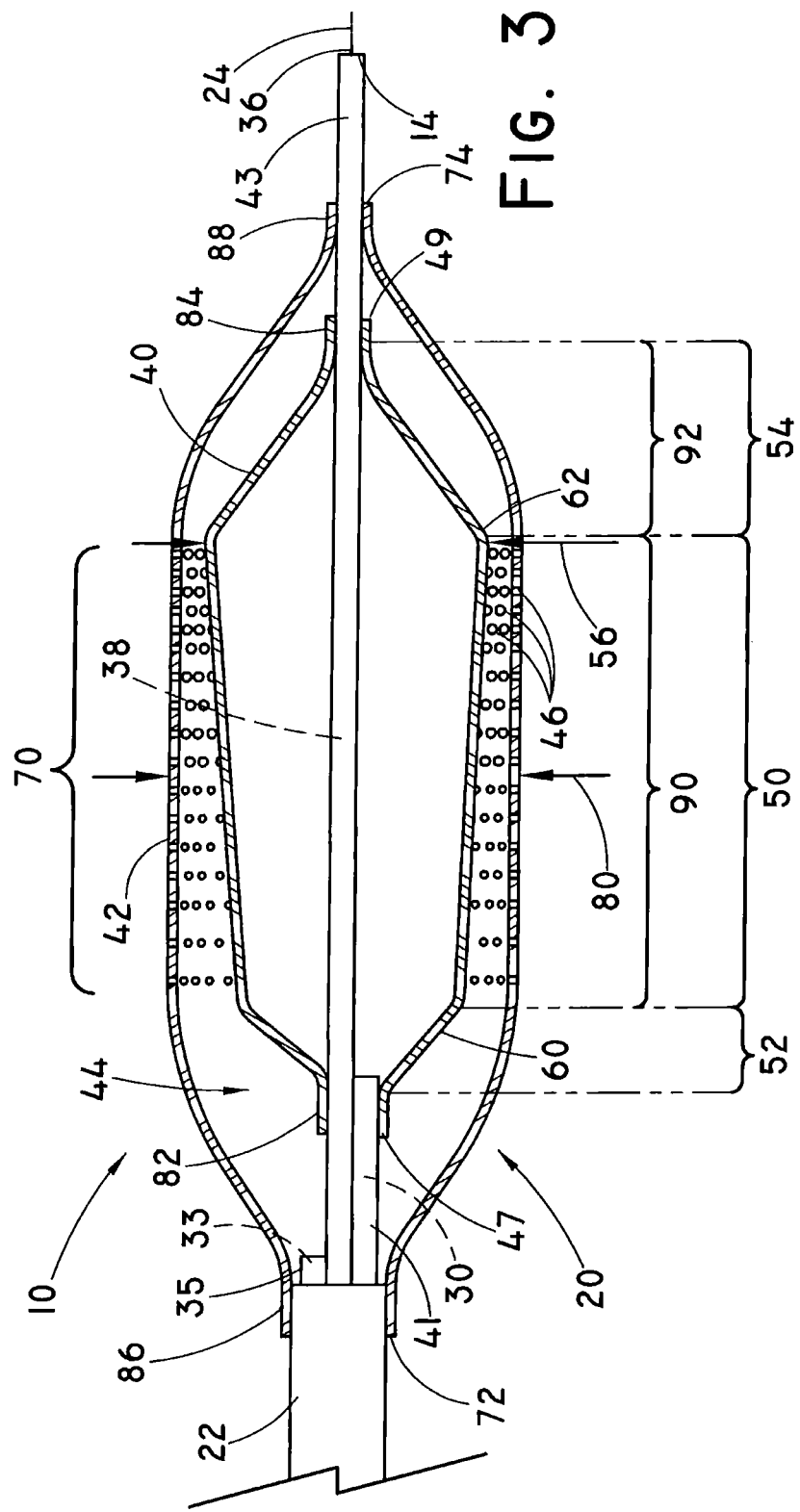
FIG. 3 is longitudinal cross-sectional view of the distal portion of the multiple-balloon catheter.

According to FIG. 3, an annular balloon fluid delivery lumen 44 for receiving a therapeutic agent or fluid, such as a diagnostic media, from the injection port 32 via the fluid delivery lumen 33 can be formed between the first balloon 40 and the second balloon 42. Both the first balloon 40 and the second balloon 42 can be sealed to the distal end of the catheter shaft 22, within the distal portion of the catheter shaft 22 housing the distal portion of the wire guide lumen 38. The multiple-balloon catheter 10 can be translated over a wire guide 36 that is shown extending from the wire guide port 23, through the catheter shaft 22 and extending through the distal end 14 of the multiple-balloon catheter 10. The multiple-balloon catheter 10 is typically provided separately from the wire guide 36, an introducer sheath (not shown) or other devices typically used to insert the multiple-balloon catheter 10 within a body vessel.

The catheter shaft 22 of the multiple-balloon catheter 10 can have any suitable dimension, but is preferably shaped and configured for the intended use in a body vessel. The catheter shaft 22 preferably includes the wire guide lumen 38 configured to house a guide wire. The lumen 38 can have an inside diameter of about approximately 0.5 mm. The overall length of the catheter shaft 22 can be approximately 110-180 cm. The catheter shaft 22 can optionally be configured as a rapid exchange catheter, such as the catheter devices described in U.S. Pat. Nos. 5,690,642 and 5,814,061. The outside diameter of the catheter shaft 22 is typically approximately 1-1.5 mm, but can be up to about 3.5 mm. Further details regarding the manufacturing and/or assembling of the catheter shaft 22 are described in U.S. PCT Application Number US2008/75970 filed on Sep. 11, 2008, incorporated herein by reference in its entirety.

Figure 2A:
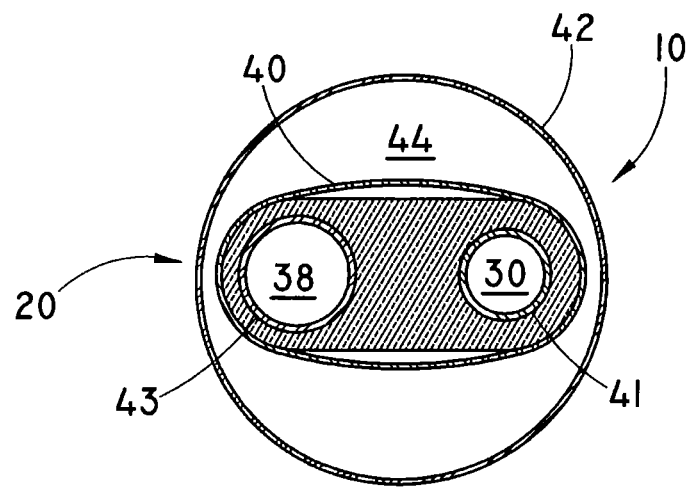
FIG. 2A is a transverse cross-sectional view along line 2A-2A of the multiple-balloon catheter shown in FIG. 1.

FIG. 2A is a transverse cross-sectional view of the multiple-balloon assembly 20 along line 2A-2A in FIG. 1 showing a proximal end of the multiple-balloon assembly 20 of the multiple-balloon catheter 10. The first balloon 40 includes a tubular member 41 defining the inflation lumen 30 and a tubular member 43 defining the wire guide lumen 38. Preferably, the inflation lumen 30 and the fluid delivery lumen 33 (not shown in FIG. 2A) are in isolation from one another. The fluid delivery lumen 33 is in fluid communication with the annular balloon fluid delivery lumen 44, which is shown between the second balloon 42 and the first balloon 40.

Figure 2B:
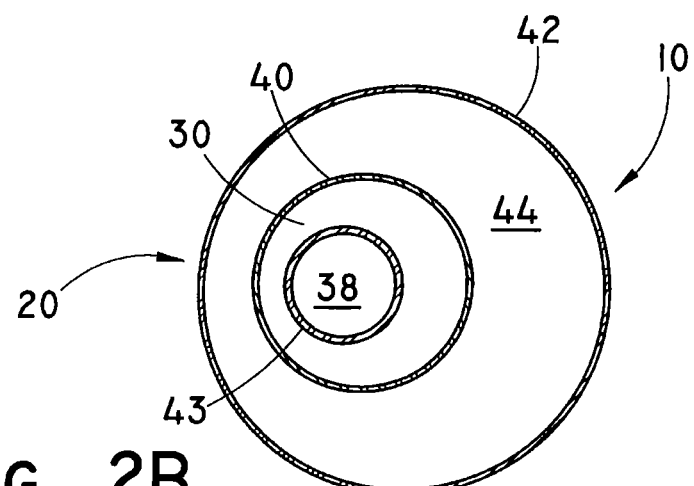
FIG. 2B is a transverse cross-sectional view along line 2B-2B of the multiple-balloon catheter shown in FIG. 1.

FIG. 2B is a transverse cross-sectional view of the multiple-balloon assembly 20 along line 2B-2B in FIG. 1 that is distally located from the line 2A-2A, showing a proximal portion of the multiple-balloon assembly 20 of the multiple-balloon catheter 10 in the inflated configuration. The first balloon 40, shown as tapered, defines the inflation lumen 30 extending radially around the tubular member 43 that defines the wire guide lumen 38. The annular balloon fluid delivery lumen 44 is shown to be in between the second balloon 42 and the first balloon 40. The cross-sectional area or diameter of the annular balloon fluid delivery lumen 44 is greater here than would be at a more distal position.

Figure 2C:
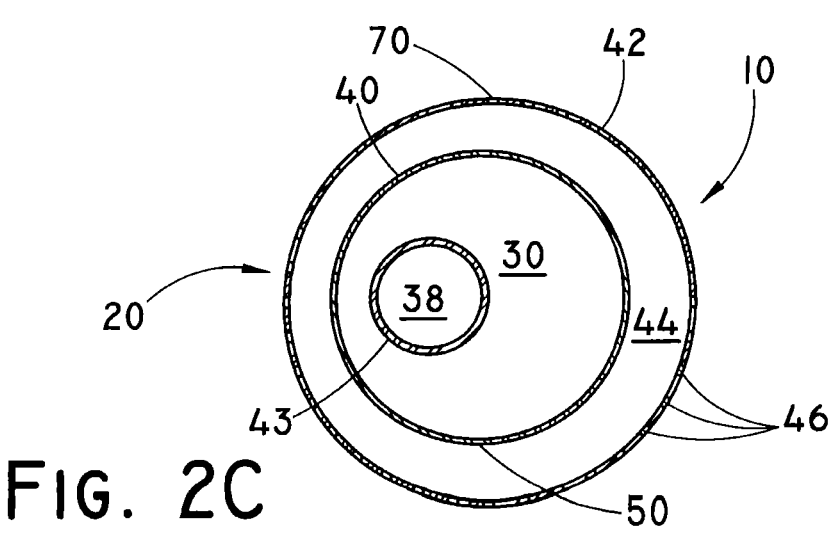
FIG. 2C is a transverse cross-sectional view along line 2C-2C of the multiple-balloon catheter shown in FIG. 1.

FIG. 2C is a transverse cross-sectional view of the multiple-balloon assembly 20 along line 2C-2C in FIG. 1 that is distally located from the line 2B-2B, showing the middle region 50 and the middle portion 70 of the multiple-balloon assembly 20 of the multiple-balloon catheter 10 in the inflated configuration. The first balloon 40, shown as tapered, defines the inflation lumen 30 extending radially around the tubular member 43 that defines the wire guide lumen 38. The holes 46 are in fluid communication with the annular balloon fluid delivery lumen 44, which is shown between the second balloon 42 and the first balloon 40. The cross-sectional area or diameter of the annular balloon fluid delivery lumen 44 is smaller here than would be at a more proximal position.

Referring to FIG. 3, the first balloon 40 having a proximal end 47 and a distal end 49 is mounted at the distal end of the catheter shaft 22. The first balloon 40 is inflatable between a deflated configuration and an inflated configuration. The inflation lumen 30 defined by the tubular member 41 of the catheter shaft 22 is in communication with the first balloon 40. The inflation of the first balloon 40 can be accomplished by any suitable means known in the art, e.g., by introducing an inflation fluid (e.g., air, saline, etc.) through the inflation lumen 30 into the first balloon 40.

The first balloon 40 has a middle region 50, which is defined between a first end 60 and a second end 62. The first balloon 40 can also have a first portion 52 and a second portion 54 contiguous with the middle region 50. The middle region 50 can be tapered or having an increasingly larger cross-sectional area or diameter in the inflated configuration along the longitudinal axis 24 moving distally away from the first end 60 to the second end 62. The middle region 50 is preferably positioned proximate the working length or middle portion 70 of the second balloon. The first portion 52 also may have an increasingly larger cross-sectional area or diameter in the inflated configuration along the longitudinal axis 24 moving distally from the proximal end 47 to the first end 60. The rate of incline of the first portion 52 may be the same as the middle region 50, or preferably, the rate of incline may be larger than the middle region 50, as shown in FIG. 3. The second portion 54, to the contrary, has an increasingly smaller cross-sectional area or diameter in the inflated configuration along the longitudinal axis 24 moving distally from the second end 62 to the distal end 49.

Figure 4:
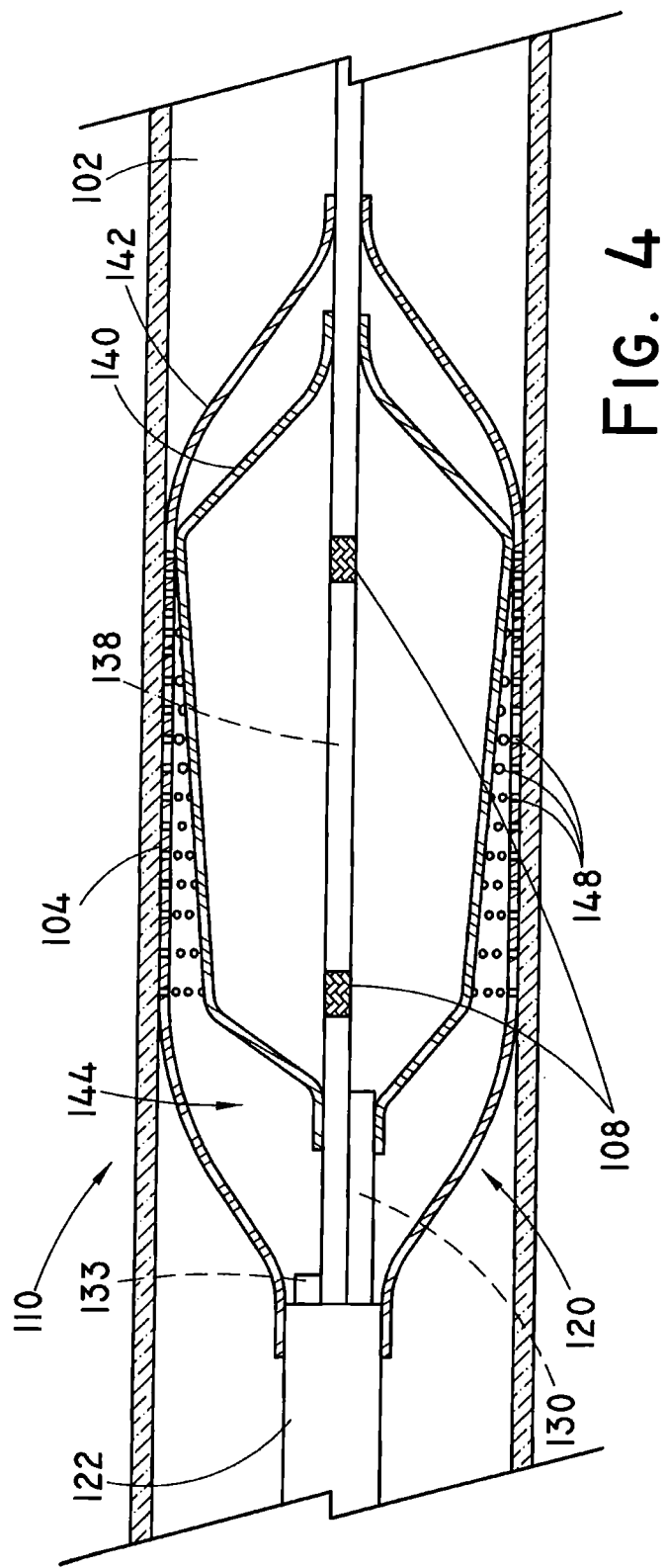
FIG. 4 is longitudinal cross-sectional view of the distal portion of a multiple-balloon catheter within a body vessel.

Preferably, the middle region 50 in the inflated configuration is tapered in a manner effective to provide a desired resistance to fluid flow through the annular balloon fluid delivery lumen 44, and/or to direct fluid flow through the annular balloon fluid delivery lumen 44 toward the holes 46 in the second balloon 42. For example, the first balloon 40 may have an outer surface having a uniform taper from the second end to the first end, as shown in FIG. 3 or FIG. 4. The angle of the taper may be selected to provide a desired rate of fluid flow through the holes 46 in the second balloon 42 as a function of the position of holes 46 relative to each other. For example, the first balloon 40 may be tapered in a manner providing for a substantially equal rate, volume, or both of fluid flow through all or substantially all of the holes 46 in the second balloon 42 at a given fluid pressure. The tapering rate of the middle region can be, for example, 0.125 mm per 10 mm in length to about 0.5 mm per 10 mm in length, although it is appreciated that the taping rate selected should be sufficient to optimize uniform delivery of fluid or therapeutic agent. In the alternative, the first balloon 40 may have an outer surface that has an asymmetric tapered configuration from the second end to the first end. This configuration can include tapering along the outer surface of the inner balloon that is parabolic, curved, a series of longitudinal portions having different degrees of tapering, or the like.

The maximum cross-sectional area or outer diameter 56 of the first balloon 40 can be large enough to dilate a portion of the body vessel when in the inflated configuration. The outer diameter 56 is preferably at the second end 62 of the middle region 50. Regardless of the configuration of the first balloon 40, when configured for use in a peripheral blood vessel, the maximum inflated outer diameter 56 of the first balloon 40 can be about 1.5 mm to about 8 mm, yet when configured for coronary vascular applications, the maximum inflated diameter 56 can have a range of from about 1.5 mm to about 4 mm. When configured for use in bile ducts, the maximum inflated outer diameter 56 of the first balloon 40 can be about 5-15 mm with a length of approximately 15-60 mm. Preferably, the geometry, material and configuration of the first balloon 40 is selected to withstand an internal inflation fluid pressure of about 5 ATM and, preferably, about 10 atmospheres without any leakage or rupture. The thickness of the first balloon 40 should be selected in order withstand a sufficient force that can inflate the first balloon 40 against the body vessel luminal wall without rupturing.

The second balloon 42 is mounted on the distal end of the catheter shaft 22. The second balloon 42 is mounted around at least a portion of the first balloon 40, but preferably mounted entirely around the first balloon 40, with the second balloon 42 enclosing the first balloon 40. The second balloon 42 includes a working length or a middle portion 70 between a proximal end 72 and a distal end 74. The second balloon 42 is moveable between a compressed configuration and an expanded configuration. Preferably, the geometry, material and configuration of the second balloon 42 are selected to withstand an internal pressure of a therapeutic agent and the inflation of the first balloon 40 without any rupture.

Referring to both the first balloon 40 and the second balloon 42 in FIG. 3, the maximum inflated outer diameter 56 of the first balloon 40 can be at a point within the second balloon 42 that is closer to the distal end 74 of the second balloon 42 than the proximal end 72 of the second balloon 42. Optionally, the maximum outer diameter 56 of the first balloon 40 can be smaller than, or substantially identical to, the maximum cross-sectional area or outer diameter 80 of the second balloon 42 in the expanded configuration. The maximum expanded outer diameter 80 of the second balloon 42 is preferably at the middle portion 70 of the second balloon 42, the cross-sectional area being large enough to dilate a portion of the body vessel when in the expanded configuration.

The second balloon 42 is preferably shaped and configured for the intended use in a body vessel. When configured for use in a peripheral blood vessel, the expanded outer diameter 80 of the second balloon 42 can be about 1.5 mm to about 8 mm, yet when configured for coronary vascular applications, the expanded outer diameter 80 can have a range of from about 1.5 mm to about 4 mm. When configured for use in bile ducts, the expanded outer diameter 80 of the second balloon 42 can be about 5-15 mm with a length of approximately 15-60 mm.

According to FIGS. 2B, 2C and 3, the annular balloon fluid delivery lumen 44 is defined as the space between the first balloon 40 and the second balloon 42. Preferably, the working region of the annular balloon fluid delivery lumen 44 is the space between the middle region 50 of the first balloon 40 and the middle portion 70 of the second balloon 42. The annular balloon fluid delivery lumen 44 is in fluid communication with the fluid delivery lumen 33, shown within a tubular member 35 of the catheter shaft 22.

The annular balloon fluid delivery lumen 44 preferably has an increasingly smaller cross-sectional area along a first portion 90 of the longitudinal axis 24 moving distally. Typically, as the first balloon 40 inflates, the volume of the annular balloon fluid delivery lumen 44 decreases, increasing the resistance or pressure loss to fluid passing through the fluid delivery lumen 33 in the distal direction. However, because the proximal portion of the annular balloon fluid delivery lumen 44 has a much larger cross-sectional area than the cross-sectional area of the distal portion of the annular balloon fluid delivery lumen 44, the proximal portion of annular balloon fluid delivery lumen 44 offers little resistance, or limited pressure loss, to fluid. Consequently, with a decrease in resistance the released therapeutic agent is permitted to move more easily in the distal direction along the second balloon 42 to reach the more distal holes 48, while maintaining an effective velocity and pressure to allow more even distribution of the therapeutic agent from the all of the holes 48. This also can permit the operator of the catheter to use a lower total pressure at the injection port 32 and/or less therapeutic agent or fluid.

Preferably, the change in cross-sectional area of the first portion 90 of the annular balloon fluid delivery lumen 44 is proportional to the tapering rate of the middle region 50 of the first balloon 40. A second portion 92 of the annular balloon fluid delivery lumen 44, contiguous with the first portion 90, can have an increasingly larger cross-sectional area along the longitudinal axis 24 moving in the distal direction. The change in cross-sectional area of the second portion 92 of the annular balloon fluid delivery lumen 44 can be proportional to the tapering rate of the second portion 54 of the middle region 50 of the first balloon 40.

The holes 46 for releasing fluid from the fluid delivery lumen 33 of the catheter shaft 22 can be disposed around the middle portion 70 of the second balloon 42. The plurality of holes 46 can have any suitable size and shape suitable to provide a desired rate of fluid release from the annular balloon fluid delivery lumen 44. Preferably, the plurality of holes 46 has a uniform dimension of about 10 micrometer (0.0004 inch) to about 1 mm (0.04 inch). This can permit the tapering rate of the annular balloon fluid delivery lumen 44 to reduce resistance to fluid delivery for a more even distribution of fluid. Alternatively, to reduce resistance to fluid delivery through the holes 46, the plurality of holes 46 can have a cross sectional area that increases in the distal direction along the outer balloon, which is shown in FIG. 1. This can include holes that increase in size and/or frequency moving distally along the second balloon 42. For example, the size of the holes can increase in the distal direction and/or the amount of holes can increase in the distal direction. The holes can be formed by any suitable method including mechanical punching, laser cutting, and the like The first balloon 40 and the second balloon 42 can be formed and/or molded from a semi-compliant expandable, biocompatible material. Preferably, the first balloon 40 and the second balloon 42 are formed from the materials having a similar Young's modulus and expandability for better maintaining the space between the balloons during the entire inflation period. For example, the balloons 40, 42 can be formed from a polyamide (e.g., nylon 12) material, a polyamide block copolymer (e.g., PEBA) and blends thereof (e.g., nylon 12/PEBA and PEBA/PEBA blends). Alternative materials include polyolefins, polyolefin copolymers and blends thereof; polyesters (e.g., poly(ethylene terephthalate), PET); polyurethane copolymers with MDI, HMDI or TDI hard segment and aliphatic polyester, polyether or polycarbonate soft segment (e.g., Pellethane, Estane or Bionate); and polyester copolymers with 4GT (PBT) hard segment and aliphatic polyester or polyether soft segments (e.g., Hytrel, Pelprene or Arnitel). The balloons 40, 42 can comprise any suitably nonelastic material such as ionomers, copolyesters, rubbers, or any medical grade polymers suitable for use in forming catheter balloons.

The proximal seal 82 and distal seal 84 of the first balloon 40 and the proximal seal 86 and distal seal 88 of the second balloon 42 can be formed in any suitable manner. Typically, the proximal and distal inner surfaces of the balloons 40, 42 are sealably attached to the catheter shaft 22 and/or tubular members to prevent any leakage of any fluid. Means of sealing the balloons 40, 42 include, for example, heat sealing, using an adhesive to form the seal, forced convection heating, radio frequency heating, ultrasonic welding, and laser bonding. Shrink tubing can be used as a manufacturing aid to compress and fuse each balloon 40, 42 to the catheter shaft 22 or the tubular member defining the wire guide lumen 38, the inflation lumen 30, and/or the fluid delivery lumen 33. The shrink tubing can be removed and disposed of after each balloon 40, 42 is sealed, or can remain on as part of the connected structure. If the catheter shaft 22 has an outer coating, each balloon 40, 42 can be bonded to the coating or directly to the catheter shaft 22.

The therapeutic agent can be delivered through the fluid delivery lumen 33 and through the annular balloon fluid delivery lumen 44 at a pressure effective to deliver the therapeutic agent to the wall of the body vessel through the holes 46 in the second balloon 42. The therapeutic agent can be delivered by direct local administration to the vessel site or injury through the holes 46 in the second balloon 42. The antisense compound can have: (i) morpholino subunits linked together by phosphorodiamidate linkages, 2 atoms long, joining the morpholino nitrogen of one subunit to the 5' exocyclic carbon of an adjacent subunit; and (ii) a sequence of bases attached to the subunits and containing a therapeutically beneficial antisense nucleotide sequence. While the compound need not necessarily 100% complementary to the target sequence, it is preferably effective to stably and specifically bind to the target sequence such that expression of the target sequence is modulated. The appropriate length of the oligomer to allow stable, effective binding combined with good specificity is about 8 to 42 nucleotide base units, and preferably about 12-25 base units. Mismatches, if present, are less destabilizing toward the end regions of the hybrid duplex than in the middle. Oligomer bases that allow degenerate base pairing with target bases are also contemplated, assuming base-pair specificity with the target is maintained. The compound preferably contains internal 3-base triplet complementary to the AUG site, and bases complementary to one or more bases 5' and 3' to the start site. One preferred compound sequence is the 20mer having the base sequence: 5'-ACG TTG AGG GGC ATC GTC GC-3', where the CAT triplet in the sequences binds to the AUG start site, the 6 bases 3' to the CAT sequence extend in the upstream (5') direction on the target, and the 11 bases 5' to the CAT sequence extend downstream on the target. This compound has enhanced solubility by virtue of having no self-annealing regions. Preferably, the therapeutic agent is a morpholino antisense compound having (i) from 8 to 42 nucleotides, including a targeting base sequence that is complementary to a region that spans the translational start codon of a c-myc mRNA; and (ii) uncharged, phosphorous-containing intersubunit linkages, in an amount effective to reduce the risk or severity of restenosis in the patient. These therapeutic agents are described in U.S. Pat. No. 7,094,765 and published U.S. patent application US 2006/0269587 A1, which are incorporated herein by reference in their entirety. While the therapeutic agent is described with respect to certain preferred antisense compounds, any suitable therapeutic agent in fluid form (i.e., a gas and/or a liquid) or in a fluid carrier can be delivered from the multi-balloon catheter assembly 20.

Referring to FIG. 4, in operation, the multiple-balloon assembly 120 of the multiple-balloon catheter 110 can be implanted within a body vessel 102 by conventional medical procedures, such as the Seldinger technique, and subsequently translated through the body vessel 102 over the wire guide through the wire guide lumen 138 to position the distal region at a point of treatment 104 therein. Once implanted, the first balloon 140 can be inflated to a desired diameter by injecting a suitable inflation fluid, such as a pressurized air, gas or liquid, through the inflation port in the manifold. For example, the first balloon 140 can be inflated to expand a stenosis in a body vessel 102 such as a coronary artery. Preferably, the first balloon 140 is inflated until the second balloon 142 contacts a portion of a wall of the body vessel 102 at the point of treatment 104.

A fluid containing a therapeutic agent and/or a diagnostic agent (e.g., x-ray contrast media) or any other fluid known to be used in a body vessel can be injected through the injection port, transported within the fluid delivery lumen 133 included in the catheter shaft 122 and introduced to the annular balloon fluid delivery lumen 144 between the second balloon 142 and the first balloon 140. The therapeutic agent fluid can be pressurized to deliver the therapeutic agent to the wall of the body vessel 102 through the plurality of holes 148 in the second balloon 142 before, during or after inflation of the first balloon 140.

Optionally, the multiple-balloon assembly 120 of the multiple-balloon catheter 110 can include radiopaque material to provide a means for locating the multiple-balloon catheter 110 within a body vessel 102. For example, the catheter shaft 122 can include one or more marker bands 108 annularly disposed around the outside of the catheter shaft 122 within the first balloon 140 to define the weeping region of the catheter 110, or where the fluid is desirably release to the body vessel. If desired, radiopaque bands can be added to the catheter shaft 122. Radiopaque marker bands 108 can be used by a clinician to fluoroscopically view and locate the distal portion of the multiple-balloon catheter 110 at a point of treatment 104 within a body vessel 102. Various configurations of radiopaque marker bands 108 can be used. For example, radiopaque marker band 108 can be located on a distal end and/or on the catheter shaft 122 within the first balloon 140. As shown, the radiopaque marker bands 108 can be stripes. Such radiopaque markers can be constructed by encapsulating a radiopaque material, such as a metallic ring, within the material of catheter shaft 122. Alternatively a portion of the catheter shaft 122 can be made radiopaque for example by constructing the portion from a radiopaque polymer. For example a polymer can be mixed with a radiopaque filler such as barium sulfate, bismuth trioxide, bismuth subcarbonate or tungsten. The radiopaque material can comprise any suitable opacifying agent, further including bismuth, tantalum, or other suitable agents known in the art. The concentration of the agent in the coating can be selected to be adequately visible under fluoroscopy.

In another embodiment, methods of delivering a therapeutic agent to a body vessel are provided using any suitable catheter configuration, including the catheter of FIG. 3 or the catheter of FIG. 4. Preferably, the methods include the step of inserting into a body vessel a multiple-balloon catheter. For example, the multiple-balloon catheter can include: (i) a catheter shaft extending from a proximal end to a distal end and defining an inflation lumen adjacently spaced from a fluid delivery lumen and a wire guide lumen; (ii) a deflated first balloon mounted on the distal end of the catheter shaft in communication with the inflation lumen, the first balloon having an increasingly larger cross-sectional area along a middle region between a first end and a second end; and (iii) a deflated second balloon mounted around at least a portion of the first balloon on the distal end of the catheter shaft in communication with the fluid delivery lumen, the second balloon having a middle portion including a plurality of holes in communication with the fluid delivery lumen for releasing a therapeutic agent from the fluid delivery lumen, where an annular balloon fluid delivery lumen is defined between the first balloon and the second balloon and in communication with the fluid delivery lumen. Optionally, the multiple-balloon catheter can be translated through the body vessel over a wire guide slidably extending through the wire guide lumen to a point of treatment. The first balloon can be inflated at the point of treatment to place the second balloon in contact with the wall of the body vessel.

With reference to FIG. 5, alternatively, the multiple-balloon catheter 150 can have a perforated outer balloon 152 radially disposed around an inner balloon 154 that has a stepped configuration. The middle region 155 of the inner balloon 154 includes a plurality of steps, for example, step 156, 158, 160, although any number of steps can be included. Each step can have a portion with a uniform cross-sectional area, a tapering cross-sectional area, or both. The general cross-sectional area of each step is increasingly larger moving along the longitudinal axis in the distal direction to define generally a taper along the outer surface of the inner balloon. The shape of the stepped inner balloon 156 affects the shape of the working region of the annular balloon fluid delivery lumen 162, providing a larger cross-sectional area at a proximal end 164 of than at a distal end 166 of the lumen 162 relative to the middle region 155. The working region of the lumen described herein in the specification refers to the portion of the lumen disposed proximate to the holes of the outer balloon. The proximal end 164 of the annular fluid delivery lumen 162 provides little resistance to the therapeutic agent, thereby allowing the therapeutic agent to flow distally with an effective velocity pressure to release from the holes 168 of the perforated outer balloon 152. This can also allow for an even distribution of fluid to the body vessel lumen between the more proximal and the more distal holes 168. In all other respects, the multiple-balloon catheter 150 including the perforated outer balloon 152 and the stepped inner balloon 154 is substantially identical to the multiple-balloon catheters 10, 110 described herein.

Alternatively, with reference to FIG. 6, a second aspect of the present invention can include a multiple-balloon catheter 210 having a perforated tapered outer balloon 212 radially disposed around an inner second balloon 214. The inner second balloon 214 can be cylindrical, but can also be tapered as described above with a suitable taper to form an increasingly larger annular lumen 216 between the first and second balloons 212, 214. This application can be important where the body vessel is known to taper, especially after natural bends of the body vessel. The perforated tapered outer balloon 212 is sized to fit the tapering rate of the body vessel, for example, 0.5 mm per 20 mm in length, although other tapering rates are within the scope of the present invention. The perforated tapered outer balloon 212 is in fluid communication with the injection port and with the fluid delivery lumen 233 through the catheter shaft 218 and separated from both the inner balloon 214 and the inflation lumen 230. The cross-sectional area or diameter of the tapered outer balloon 212 is increasingly smaller moving distally. The tapered outer balloon includes a plurality of holes 215. Alternatively, the cross-sectional area or diameter of the tapered outer balloon can be increasingly larger moving distally, and this will depend on the orientation of the body vessel and the location of the point of insertion in the body.

The inner balloon 214 is preferably non-porous and can be a variety of shapes such that the shape of the tapered outer balloon 212 relative to the shape of the inner balloon 214 affects the shape of the working region 252 of the annular balloon fluid delivery lumen 216, providing a larger cross-sectional area at the proximal end 220 than at the distal end 222 of the working region 252 of the lumen 216. The inner balloon can be cylindrical or can have a generally taper such as described in the above Figures. When in the inflated configuration the inner balloon 214 can include a tapering surface between proximal and distal conical ends of the balloon having an increasingly smaller cross-sectional area along the middle region 250 from the first end 262 to the second end 260. The taper of the tapering surface of the outer balloon 212 along its middle portion or working length 270 from the first end 271 to the second end 273, which is between proximal and distal conical ends of the balloon can be greater than the taper of the tapering surface of the inner balloon 214, as shown in FIG. 6, in order for the cross-sectional area of the annular lumen 216 to become increasingly smaller. It is desirable that the proximal end 220 of the working region 252 of the annular fluid delivery lumen 216 provides little resistance to the therapeutic agent or fluid, thereby allowing the therapeutic agent to flow distally with an effective velocity pressure to release from the holes 215 of the perforated tapered outer balloon 212. This can also allow for an even distribution of fluid to the body vessel lumen between the more proximal and the more distal holes 215. In all other respects, the multiple-balloon catheter 210 including the perforated tapered outer balloon 212 and the tubular or tapered inner balloon 214 is substantially identical to the multiple-balloon catheters 10, 110 described herein. For instance, the middle portion 270 of the outer balloon 212 can include a plurality of holes 215 having a combined cross-sectional area that increases from the first end 270 to the second end 273 of the middle portion of the outer balloon. This can include holes that increase in size, density and/or frequency in order for the combined cross-sectional area to increase in the distal direction. Further, in the inflated configuration the inner balloon 214 has a maximum cross-sectional area at the first end 262 that is sized to dilate a portion of said body vessel.

Figure 7A:
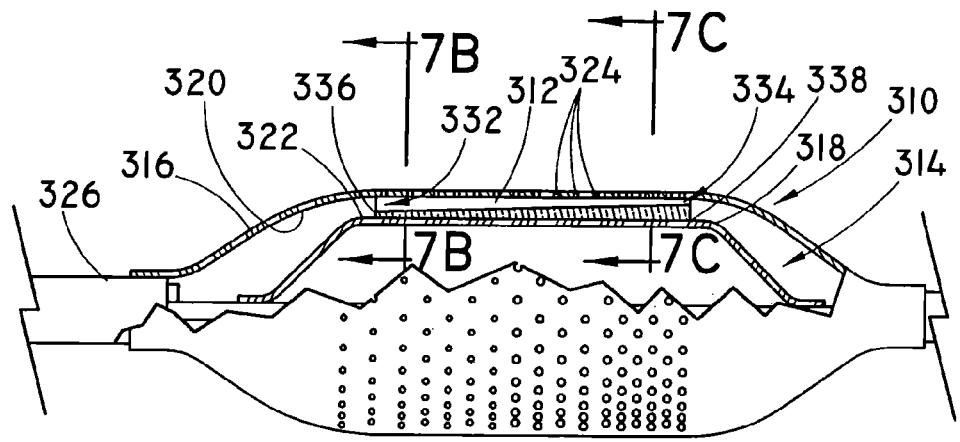
FIG. 7A is a side view of another multiple-balloon catheter, depicting raised portions in between the inner and outer balloons.
Figure 7B:
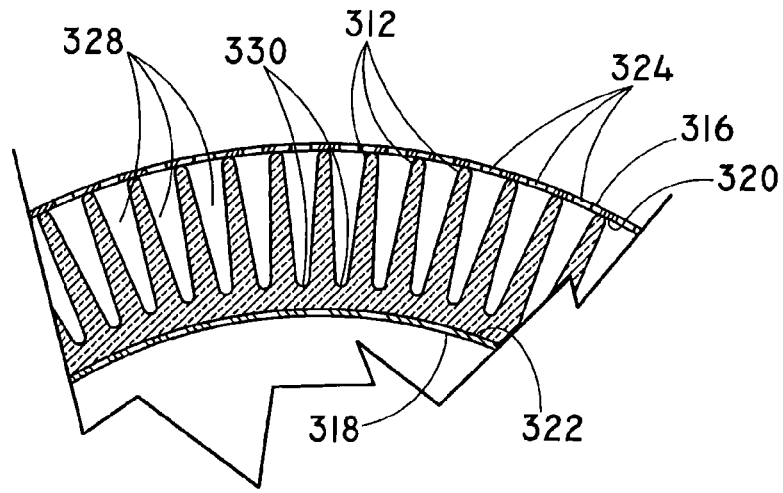
FIG. 7B is a partial sectional view taken along line 7B-7B in FIG. 7A, depicting raised portions and channels.
Figure 7C:
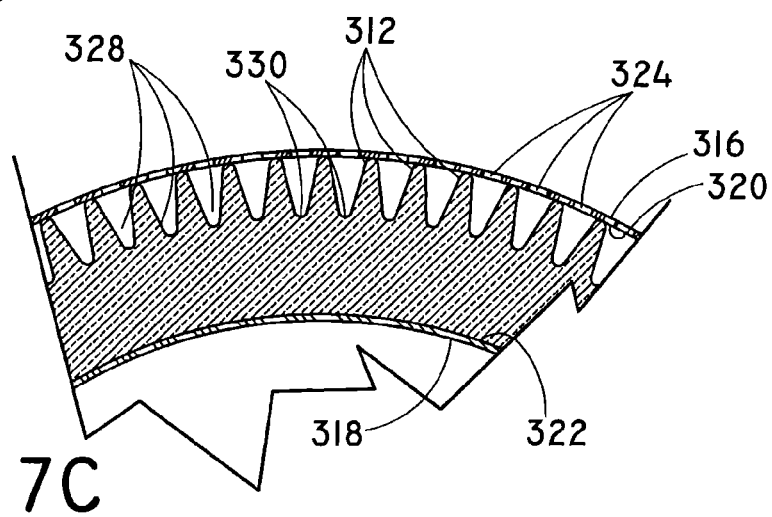
FIG. 7C is a partial sectional view taken along line 7C-7C in FIG. 7A, which is distal to line 7B-7B, depicting raised portions and channels.

In a third aspect of the present invention, with reference to FIGS. 7A-C, the multiple-balloon catheter 310 can include one or more roughened or raised surface portions 312. The raised portions 312 are formed integrally with one of the balloons 316, 318 or attached to either of the balloons, or both. The raised portions 312 are disposed within the annular fluid delivery lumen 314 between an outer balloon 316 and an inner balloon 318. For example, the inner surface 320 of the outer balloon 316 and/or the outer surface 322 of the inner balloon 318 may include bumps, nodes or other surface features to form surface portions 312 that direct or channel fluid moving through the fluid delivery lumen toward one or more holes 324 in the outer balloon 316. The raised portions can be uniform in height along the balloons or may vary in height such that the raised portions taper to a greater height in the distal direction.

In one embodiment, a perforated outer balloon 316 may be radially disposed around an inner balloon 318 having raised surface portions 312, such as nodes, bumps, or some other form of raised irregularities, aligned linearly on the outer surface 322 of the inner balloon 318. Preferably, the raised portions are disposed circumferentially around the annular lumen 314, as shown in FIGS. 7B and 7C. FIG. 7B is a partial sectional view taken along line 7B-7B in FIG. 7A, and FIG. 7C is a partial sectional view taken along line 7C-7C in FIG. 7A, which is distal to line 7B-7B. The inner balloon 318 is preferably non-porous and in fluid communication with the inflation port through the body of the catheter shaft 326. When the inner balloon 318 is inflated, the top surfaces of the raised surface portions 312 or irregularities sealably engage the underneath surface 320 of the outer balloon 316 to form channels 328 or passageways through which a therapeutic agent or fluid can be delivered, as shown in FIGS. 7B and 7C.

Preferably, the channels 328 have a increasingly smaller cross-sectional area along a portion of the longitudinal axis moving distally to permit more uniform distribution of the fluid exiting the holes as described herein. The change in cross-sectional area of the channels could be various means as described herein, for example, a uniform taper, asymmetric taper, stepped configuration or the like. Each of the raised portions 312 can be interconnected by a web 330 along the outer surface 322 of the inner balloon 318. The web 330 can have a cross-sectional area defined by the bottom of the channel to the surface of the inner balloon. The cross-sectional area may be uniform along the length of the balloons. Preferably, the web 330 has a cross-sectional area at a first point 332 and a cross-sectional area at a second point 334 distal to the first point 332. The cross-sectional area at the second point 334 is greater than the cross-sectional area at the first point 332 such that the channel 328 becomes narrower, or has less depth, in the distal direction, as illustrated in FIGS. 7B and 7C.

Optionally, each of the raised portions 312 can have a lateral cross-sectional area at the first point 332 and a lateral cross-sectional area at the second point 334 distal to the first point. The lateral cross-sectional area at the second point 334 being greater than the lateral cross-sectional area at the first point 332 to define channels 328 that become narrower, or have less width, along the distal direction. The width of the webs can also vary along the length of the channel. Alternatively, the cross-sectional area of the channels can change based on the depth, width, or both.

The formed channels can be straight or can taper, funneling the fluid from the proximal end 336 where the cross-sectional area of the channel 328 is larger to the distal end 338 where the cross-sectional area of the channel 328 is smaller. The channels 328 can be a variety of shapes such as V-shaped, U-shaped, sinusoidal or wavy, or other like shapes and can have a closed end and/or open end at the distal portion of the channel, or various combinations of both. For example, the channels 328 shown in FIGS. 7B and 7C are V-shaped and have a closed end. The channels 328 are preferably molded with the molding of the balloon, but can be separate structures that are attached to the surface with adhesions or heat welding. The channels 328 can not only direct the fluid to the holes 324 of the perforated outer balloon 316, but also allow an increase in velocity and/or pressure of fluid to all of the holes 324 of the perforated outer balloon 316.

The holes 324 are preferably created in the outer balloon where the channels are located. This can aid in the release of the fluid from the holes 324 and allow for an even distribution of fluid to the body vessel lumen between the more proximal and the more distal holes 324. Although the raised surface portions 312 are described in relation to outer surface 322 of the inner balloon 318, it is appreciated that the raised surface portions 312 can be a part of the inner surface 320 of the outer balloon 316 or part of both of the inner surface of the outer balloon and the outer surface of the inner balloon. In all other respects, the multiple-balloon catheter 310 including one or more roughened or raised surface portions 312 is similar or identical to the multiple-balloon catheters 10, 110 described herein.

Those of skill in the art will appreciate that other embodiments and variants of the structures and methods described above can be practiced within the scope of the present invention. It is therefore intended that the foregoing detailed description be regarded as illustrative rather than limiting, and that it be understood that it is the following claims, including all equivalents, that are intended to define the spirit and scope of this invention.

I claim:

1. A balloon catheter comprising:
a catheter shaft extending along a longitudinal axis;
a first balloon mounted on the catheter shaft, the first balloon having a first portion attached to the catheter shaft, a second portion disposed distal of the first portion and attached to the catheter shaft, and a middle working region disposed from the first portion to the second portion, the first portion having an increasingly larger cross-sectional area along the longitudinal axis in a distal direction, the second portion having an increasingly smaller cross-sectional area along the longitudinal axis in the distal direction, the first portion and the second portion joined to one another by the middle working region; and
a second balloon mounted around at least a portion of the first balloon, the second balloon having a middle working length, and a plurality of holes formed in the middle working length to define a perforated portion of the middle working length, the plurality of holes consisting of all of the holes through the second balloon, each of the first and second balloons movable to an expanded configuration to define an annular space therebetween, the annular space being in communication with the plurality of holes of the second balloon,
the annular space being disposed between the perforated portion of the middle working length of the second balloon and a corresponding portion of the middle working region of the first balloon, the annular space being defined by a length extending between a first end disposed at a most proximal hole of the plurality of holes of the second balloon and a second end disposed at a most distal hole of the plurality of holes of the second balloon, wherein said annular space has an increasingly smaller cross-sectional area along the longitudinal axis in the distal direction along the length from the first end to the second end of the annular space.

2. The balloon catheter of claim 1, wherein the middle working length of the second balloon has a substantially uniform cross-sectional area along the longitudinal axis in the distal direction.

3. The balloon catheter of claim 1, wherein the portion of the middle working region of the first balloon corresponding to the perforated portion of the second balloon has an increasingly larger cross-sectional area along the longitudinal axis in the distal direction.

4. The balloon catheter of claim 1, wherein the portion of the middle working region of the first balloon corresponding to the perforated portion of the second balloon has a cross-sectional area that decreases along the longitudinal axis in the distal direction.

5. The balloon catheter of claim 4, wherein the perforated portion of the second balloon has a cross-sectional area that decreases along the longitudinal axis in the distal direction.

6. The balloon catheter of claim 5, wherein a rate of decrease of the cross-sectional area of the perforated portion of the second balloon is greater than a rate of decrease of the cross-sectional area of the portion of the middle working region of the first balloon corresponding to the perforated portion of the second balloon.

7. The balloon catheter of claim 1, wherein the middle working region of the first balloon has a taper that is generally uniform along the longitudinal axis from the first end of the annular space to the second end of the annular space.

8. The balloon catheter of claim 1, wherein the middle working region of the first balloon comprises a series of steps each having a different cross-sectional area.

9. The balloon catheter of claim 8, wherein the series of steps includes a first step having a first cross-sectional area and a second step having a second cross-sectional area and positioned distal to the first step, the second cross-sectional area of the second step being greater than the first cross-sectional area of the first step.

10. The balloon catheter of claim 1, wherein the second balloon comprises a first portion attached to the catheter shaft and a second portion disposed distal of the first portion and attached to the catheter shaft, the first portion having an increasingly larger cross-sectional area along the longitudinal axis in the distal direction, the second portion having an increasingly smaller cross-sectional area along the longitudinal axis in the distal direction, wherein the middle working length of the second balloon is positioned longitudinally between the first portion and the second portion thereof.

11. The balloon catheter of claim 1, wherein the annular space extends longitudinally along a majority of a length of the middle working length of the second balloon.

12. A balloon catheter comprising:
a catheter shaft extending along a longitudinal axis and configured to carry a first fluid and a second fluid;
a first balloon mounted on the catheter shaft and expandable with introduction of the first fluid therein, the first balloon having a first portion attached to the catheter shaft, a second portion disposed distal of the first portion and attached to the catheter shaft, and a middle region positioned from the first portion to the second portion of the first balloon, the first portion and the second portion of the first balloon joined to one another by the middle region, the first portion having an increasingly larger cross-sectional area along the longitudinal axis in a distal direction, the second portion having an increasingly smaller cross-sectional area along the longitudinal axis in the distal direction; and
a second balloon mounted around at least a portion of the first balloon, the second balloon having a middle portion, a plurality of holes formed in the middle portion to define a perforated portion of the middle portion, the plurality of holes consisting of all of the holes through the second balloon;
the first and second balloons in an expanded configuration structured and arranged to define an annular lumen therebetween, the annular lumen being in communication with the plurality of holes of the second balloon, the annular lumen configured to allow the second fluid to pass therethrough and out the holes,
the annular lumen having a tapered working region extending longitudinally adjacent the perforated portion of the middle portion of the second balloon and a corresponding portion of the middle region of the first balloon, the annular lumen being defined by a length extending between a first end disposed longitudinally between the first portion and the second portion of the first balloon and at a most proximal hole of the plurality of holes of the second balloon, and a second end disposed distal of the first end and longitudinally between the first portion and the second portion of the first balloon and at a most distal hole of the plurality of holes of the second balloon, wherein the tapered working region has a cross-sectional area that decreases along the longitudinal axis in the distal direction along the length from the first end to the second end of the annular lumen.

13. The balloon catheter of claim 12, wherein the middle portion of the second balloon has a substantially uniform cross-sectional area along the longitudinal axis in the distal direction.

14. The balloon catheter of claim 12, wherein the middle region of the first balloon has an increasingly larger cross-sectional area along the longitudinal axis in the distal direction.

15. The balloon catheter of claim 12, wherein the portion of the middle region of the first balloon corresponding to the perforated portion of the second balloon has a cross-sectional area that decreases along the longitudinal axis in the distal direction.

16. The balloon catheter of claim 15, wherein the perforated portion of the second balloon has a cross-sectional area that decreases along the longitudinal axis in the distal direction.

17. The balloon catheter of claim 16, wherein a rate of decrease of the cross-sectional area of the perforated portion of the second balloon is greater than a rate of decrease of the cross-sectional area of the portion of the middle region of the first balloon corresponding to the perforated portion of the second balloon.

18. The balloon catheter of claim 12, wherein the middle region of the first balloon has a generally uniform taper along the longitudinal axis from the first end of the annular lumen to the second end of the annular lumen.

19. The balloon catheter of claim 12, wherein the middle region of the first balloon comprises a series of steps each having a different cross-sectional area.

20. A method of delivering a fluid to a treatment site within a body vessel, the method comprising:
translating a balloon catheter to the treatment site within the body vessel, the balloon catheter comprising a first balloon coupled to a shaft and comprising a middle working region, a first portion contiguous with a first end of the middle working region, and a second portion positioned distal of the first portion and contiguous with a second end of the middle working region, the middle working region disposed from the first portion to the second portion, the first portion attached to the shaft and comprising an increasingly larger cross-sectional area along a longitudinal axis in a distal direction, the second portion attached to the shaft and comprising an increasingly smaller cross-sectional area along the longitudinal axis in the distal direction, a second balloon coupled to the shaft at least partially around the first balloon, the second balloon having a plurality of holes formed therein to define a perforated portion of the second balloon, the plurality of holes consisting of all of the holes through the second balloon, the first and second balloons structured and arranged in an expanded configuration to define an annular lumen therebetween, the annular lumen in communication with the plurality of holes and being disposed between the perforated portion of the second balloon and a corresponding portion of the first balloon, the annular lumen being defined by a length extending between a first end disposed at a most proximal hole of the plurality of holes of the second balloon and a second end disposed at a most distal hole of the plurality of holes of the second balloon, wherein said annular lumen has an increasingly smaller cross-sectional area along the longitudinal axis in the distal direction along the length from the first end to the second end of the annular lumen;

expanding the first balloon to the expanded configuration; and introducing a fluid into the annular lumen between the first and second balloons to deliver the fluid through the plurality of holes of the second balloon to the treatment site of the body vessel.

* * * * *